US009854804B2

(12) United States Patent
Kim et al.

(10) Patent No.: US 9,854,804 B2
(45) Date of Patent: Jan. 2, 2018

(54) ANTIFUNGAL COMPOSITION COMPRISING POLYCYCLIC PEPTIDE COMPOUND AND METHOD FOR PREPARING THE SAME

(75) Inventors: Won Gon Kim, Daejeon (KR); Yun Ju Kwon, Daejeon (KR); Mi Jin Sohn, Daejeon (KR)

(73) Assignee: KOREAN RESEARCH INSTITUTE OF BIOSCIENCE AND BIOTECHNOLOGY, Daejeon (KR)

( * ) Notice: Subject to any disclaimer, the term of this patent is extended or adjusted under 35 U.S.C. 154(b) by 1113 days.

(21) Appl. No.: 13/978,488

(22) PCT Filed: Jan. 4, 2012

(86) PCT No.: PCT/KR2012/000097
§ 371 (c)(1),
(2), (4) Date: Oct. 2, 2013

(87) PCT Pub. No.: WO2012/093859
PCT Pub. Date: Jul. 12, 2012

(65) Prior Publication Data
US 2014/0030242 A1    Jan. 30, 2014

(30) Foreign Application Priority Data

Jan. 4, 2011 (KR) .................. 10-2011-0000492

(51) Int. Cl.
*A01N 43/90* (2006.01)
*C07K 7/06* (2006.01)
*C07K 7/54* (2006.01)
*A61K 31/404* (2006.01)

(52) U.S. Cl.
CPC ............ *A01N 43/90* (2013.01); *A61K 31/404* (2013.01); *C07K 7/06* (2013.01)

(58) Field of Classification Search
None
See application file for complete search history.

(56) References Cited

U.S. PATENT DOCUMENTS 5,140,101 A   8/1992   Oka et al.
6,365,571 B1  4/2002   Masuda et al.

FOREIGN PATENT DOCUMENTS

JP    03-264535 A    11/1991

OTHER PUBLICATIONS

Preobrazhenskaya et al., Polycyclic peptide and glycopeptide antibiotics and their derivatives as inhibitors of HIV entry, Antiviral Research, 2006, vol. 71, pp. 227-236.*
Francis. CID, 2005, 40, 100-107.*
Organic isomers, http://faculty.lacitycollege.edu/boanta/LAB102/Organic%20Isomers.htm, accessed May 12, 2015.*
Kaneko et al. (1989). Complestatin, A Potent Anti-Complement Substance Produced by Streptomyces Lavendulae. *The Journal of Antibiotics*, 42:236-241.
Kobayashi et al. (2001). Neuroprotectins A and B, Bicyclohexapeptides Protecting Chick Telencephalic Neuronal Cells from Excitotoxicity, I. Fermentation, Isolation, and Physicochemical Properties and Biological Activities. *The Journal of Antibiotics*, 54(12):1013-1018.
Singh et al. (2001). The Complestatins as HIV-1 Integrase Inhibitors. Efficient Isolation, Structure Elucidation, and Inhibitory Activities of Isocomplestatin, Chloropeptin I, new Complestatins, A and B, and Acid-Hydrolysis Products of Chloropeptin I. *Journal of Natural Products*, 54(7):874-882.
Tanka et al. (1997). Chloropeptins, New Anti-HIV Antibiotics Inhibiting gp120-CD4 Binding from *Streptomyces* sp. I. Taxonomy, Fermentation, Isolation, and Physico-chemical Properties and Biological Activities. *The Journal of Antibiotics*, 50(1):58-65.
International Search Report, dated Sep. 5, 2012 in connection with PCT International Application No. PCT/KR2012/000097, filed Jan. 4, 2012 [including English language translation].

\* cited by examiner

*Primary Examiner* — Noble E Jarrell
(74) *Attorney, Agent, or Firm* — John P. White; Cooper & Dunham LLP

(57) ABSTRACT

Disclosed are a novel strain with antibacterial activity, identified as *Streptomyces* sp. AN1542 strain (Accession No.: KCTC 12113BP), an antibacterial composition comprising a compound represented by Chemical Formula 1 or 2, or a strain producing the same as an active ingredient, and a method for producing the same. Exhibiting potent antibacterial activity against pathogenic microbes and antibiotic-resistant microbes, particularly, MRSA, QRSA, VRSA and VRE, the compound or the strain of the present invention can be applied to the treatment of infectious diseases caused by superbacteria.

10 Claims, 2 Drawing Sheets

[Figure 1]
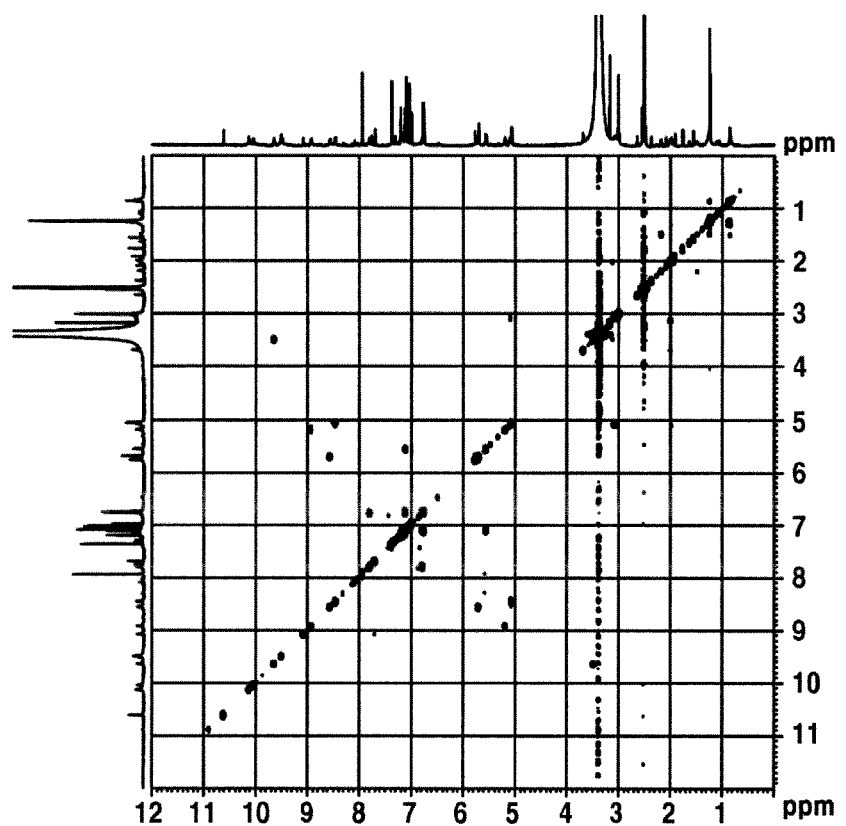

[Figure 2]
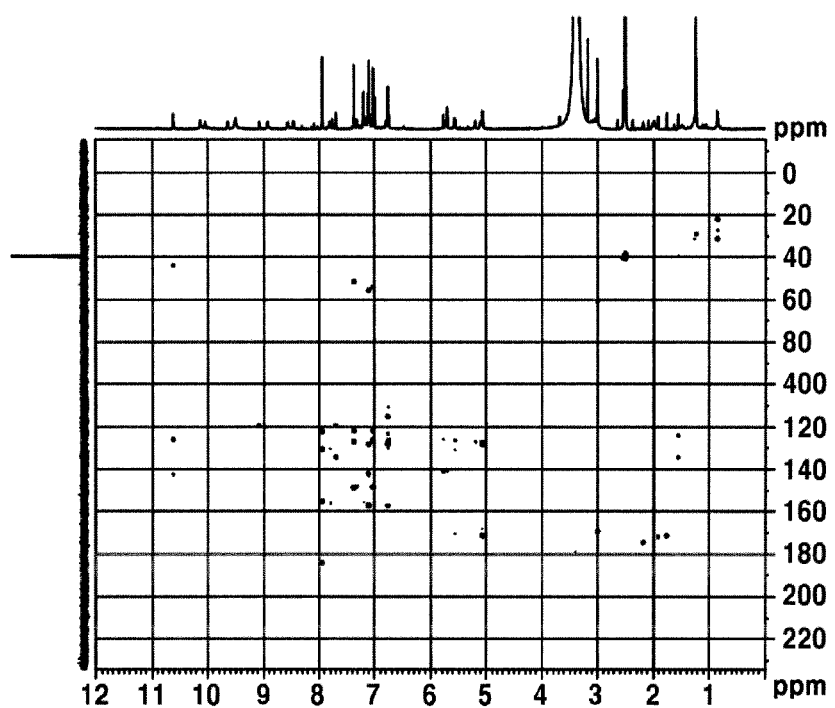

ANTIFUNGAL COMPOSITION COMPRISING POLYCYCLIC PEPTIDE COMPOUND AND METHOD FOR PREPARING THE SAME

TECHNICAL FIELD

The present invention relates to a novel strain with antibacterial activity, identified as *Streptomyces* sp. AN1542 strain (Accession No.: KCTC 12113BP), and an antibacterial composition comprising a compound represented by Chemical Formula 1 or 2, or a strain producing the same as an active ingredient. Also, the present invention relates to a method for the prevention and treatment of a disease caused by microbial infections, a method for exerting a microbicidal or microbiostatic effect, and a method for producing the preceding compound.

BACKGROUND ART

In general, the direct or indirect damage caused by pathogenic microbes gives rise to large and severe economical, environmental and medical problems. For example, the decomposition of food during circulation is one of the greatest problems in the food industry while the excess use of chemical microbicides which produce environmental pollution, with microbicide residue on crops negatively affecting the health of consumers becomes problematic in the agricultural industry. In addition, the emergence of resistant strains resulting from the misuse and overuse of antibiotics has caused serious medical and social problems. Although proper antibiotic therapy in the treatment of infectious diseases is one of the most important factors that determine the prognosis of patients, it has been more difficult to utilize effective antibiotics due to the emergence of strains resistant against antibiotics.

For instance, Vancomycin has traditionally been reserved as a drug of "last resort" for treatment of infection by *Staphylococcus* strains, which are the most common causes of infection of humans. However, Methicillin-resistant *S. aureus* (MRSA) which can be treated only by Vancomycin broke out in the 1970s. Since then, Vancomycin-resistant *Entrococcus* (VRE) was first found in Europe in 1998, followed by the discovery of Vancomycin intermediate-resistant *S. aureus*, (VISA) in Japan, the United States, France, and Korea in the late 1990s. In 2002, furthermore, the US Centers for Disease Control first reported the presence of Vancomycin-resistant *Staphylococcus aureus* (VRSA), which is highly resistant to Vancomycin, creating an alarming likelihood of the spread of so-called "superbacteria." Therefore, antibiotic resistance is becoming a worldwide crisis and there is a pressing need for a novel approach to antibiotics.

DISCLOSURE

Technical Problem

Culminating in the present invention, intensive and thorough research into antibacterial substances obtainable from natural sources, such as antimicrobes, plants, etc., for use against superbacteria, has resulted in the finding that a *Streptomyces* sp. AN1542 strain (Accession No.: KCTC 12113BP) with antibacterial activity, polycyclic peptide compounds complestatin and neuroprotectin A or a strain producing the same have potent antibacterial activity against superbacteria, such as Vancomycin-resistant bacteria.

Technical Solution

It is an object of the present invention to provide a *Streptomyces* sp. AN1542 strain (Accession No.: KCTC 12113BP).

It is another object of the present invention to provide an antibacterial composition, comprising at least one of a compound represented by Chemical Formula 1 or 2, an isomer, derivative or pharmaceutically acceptable salt thereof, or a strain producing a compound represented by the following Chemical Formula 1 or 2, a spore, mycelium or cell culture thereof.

It is a further object of the present invention to provide a method for preventing or treating an infectious disease caused or triggered by a microbe, comprising administering a therapeutically effective amount of the antibacterial composition to a subject in need thereof.

It is still a further object of the present invention to provide a method for producing a compound represented by Chemical Formula 1 or 2, or an isomer, derivative or pharmaceutically acceptable salt thereof, comprising allowing *Streptomyces* sp. AN1542 strain (Accession No.: KCTC 12113BP) to produce the compound represented by the following Chemical Formula 1 or 2.

Advantageous Effects

Exhibiting potent antibacterial activity against pathogenic microbes and antibiotic-resistant microbes, particularly against MRSA-, QRSA-, and Vancomycin-resistant bacteria VRSA and VRE, the compound or the strain of the present invention can be utilized in the treatment of infectious diseases caused by superbacteria.

DESCRIPTION OF DRAWINGS

FIG. 1 shows 1H-1H COSY data of neuroprotectin A according to one embodiment of the present invention.

FIG. 2 shows HMBC spectral data of neuroprotectin A according to one embodiment of the present invention.

BEST MODE

In accordance with an aspect thereof, the present invention relates to a *Streptomyces* sp. AN1542 strain (Accession No.: KCTC 12113BP) with antibacterial activity.

Mutations of the *Streptomyces* sp. AN1542 strain (Accession No.: KCTC 12113BP) of the present invention fall within the scope of the present invention. Among the mutations are naturally occurring mutations, and mutations changed by physical stimuli (e.g., UV light), or chemical mutagens (e.g., base compounds). So long as it exerts antibacterial activity by producing the compound of Chemical Formula 1 or 2, for example, any mutation is within the scope of the present invention.

In an aspect of the present invention, strains with potent antibacterial activity were isolated after separating bacteria, fungi, and actinomyces from soil across South Korea, and subjected to mycological study. The strain thus obtained was classified as a typical actinomyces in morphology as observed by microscopy. From the strain, its whole genome was separated, and used to clone 16S ribosomal DNA by PCR. Analysis of the full sequence of the rRNA identified the strain as a *Streptomyces*, which was called *Streptomyces* sp. AN1542 and deposited with KCTC (the Korean Collection for Type Cultures) of the Korea Research Institute of Bioscience and Biotechnology (KRIBB) on Jan. 3, 2012 (Accession No.: KCTC 12113BP).

In accordance with another aspect thereof, the present invention addresses an antibacterial composition, comprising at least one of a compound represented by the following Chemical Formula 1 or 2, an isomer, derivative or pharmaceutically acceptable salt thereof, or a strain producing a compound represented by the following Chemical Formula 1 or 2, a spore, mycelium or cell culture thereof.

The term "strains," as used herein, is intended to include any strain that produces complestatin or neuroprotecting A. Spores, mycelium or cell cultures of the strain can also be used.

The compounds of the present invention may be synthesized using a typical method known in the art or may be obtained as natural compound produced from the strains of interest. Preferably, the compounds of the present invention may be produced from *Streptomyces* sp. strain, and more

[Chemical Formula 1]

[Chemical Formula 2]

The compounds of Chemical Formula 1 and 2 are polycyclic peptides which are respectively referred to as complestatin and neuroprotectin A. In addition to complestatin and neuroprotectin A, their isomers, derivatives or pharmaceutically acceptable salts are within the scope of the present invention.

As used herein, the term "isomers" refers to the relationship between compounds with the same molecular formula having different chemical structures. There are many different classes of isomers, such as structural isomers, geometrical isomers, optical isomers and geometrical isomers. Stereoisomers are compounds that have the same chemical composition but differ in the arrangement of their atoms and functional groups in space. Optical isomers (enantiomers) are two stereoisomers of one compound which are non-superposable mirror images of each other. Diastereomers are stereoisomers that have two or more of chiral centers and are not mirror images of each other.

As used herein, the term "derivatives" is intended to refer to compounds obtained by replacing a structural part of complestatin or neuroprotectin A with other atoms or atomic groups. The term "pharmaceutically acceptable salts," as used herein refers to relatively non-toxic inorganic and organic acid salts.

preferably from *Streptomyces* sp. AN1542 strain (Accession No.: KCTC 12113BP). In the present invention, complestatin and neuroprotectin A were isolated from *Streptomyces* sp. AN1542 strain (Accession No.: KCTC 12113BP) and was first identified as having potent antibacterial activity against microbes resistant to conventional antibiotics.

In addition, the strain of the present invention may preferably be a *Streptomyces* sp. strain, and more preferably *Streptomyces* sp. AN1542 strain (Accession No.: KCTC 12113BP).

Preferably, the composition of the present invention exhibits antibacterial activity against any one or more selected from the group consisting of *Staphylococcus aureus, Bacillus subtilis, Bacillus cereus, Staphylococcus epidermis, Enterococcus faecium*, Methicillin-resistant *Staphylococcus aureus* (MRSA), Quinolone-resistant *Staphylococcus aureus* (QRSA), Vancomycin-resistant *Staphylococcus aureus*, and Vancomycin-resistant *Enterococcus*.

In one embodiment of the present invention, complestatin and neuroprotectin A, both isolated from the *Streptomyces* sp. of the present invention, together with the conventional antibacterial agents vancomycin and oxacillin, were examined for antibacterial activity against *Staphylococcus aureus, Bacillus subtilis, Bacillus cereus, Staphylococcus epidermis, Enterococcus faecium*, Methicillin-resistant *Staphylococcus aureus* (MRSA) and Quinolone-resistant *Staphylococcus aureus* (QRSA). Analysis data showed that both complestatin and neuroprotectin A have antibacterial activity identical or superior to that of Vancomycin against the preceding bacteria (MIC of 0.5-2 µg/ml), and particularly against MRSA and QRSA (Example 4 and Table 3).

In one embodiment of the present invention, an examination was also made of the antibacterial activity of the compounds isolated from the *Streptomyces* sp. of the present invention, together with the conventional antibiotics vancomycin and oxacillin, against vancomycin-resistant bacteria. The compounds of the present invention, complestatin and neuroprotectin A, exhibited strong antibacterial activity against the vancomycin resistant bacteria Vancomycin-resistant *S. aureus* (VRSA) and Vancomycin-resistant *Enterococcus* (VRE) (MIC of 1 µg/ml, Example 5 and Table 4) whereas neither vancomycin nor oxacillin, even at 200 µg/ml, exhibited antibacterial activity against VRSA and VRE.

Preferably, the antibacterial composition of the present invention may be a pharmaceutical composition.

The antibacterial composition of the present invention may further comprise one or more well-known active ingredients with antibacterial activity against pathogenic microbes or resistant bacteria in addition to the compounds of the present invention.

Also, the antibacterial composition of the present invention may further comprise a pharmaceutically acceptable carrier.

As used herein, the term "pharmaceutically acceptable carrier" refers to a pharmaceutically acceptable material, composition or vehicle, such as a liquid or solid filler, a diluent, an excipient, a solvent or a capsulation material, which is involved in the conveyance or transportation of a composition or ingredient of interest from one organ or part of the body to another target organ or part of the body. For administration, the composition of the present invention may further comprise a pharmaceutically acceptable carrier, excipient, or diluent in addition to the above-mentioned active ingredient. Examples of the carrier, the excipient and the diluent include lactose, dextrose, sucrose, sorbitol, mannitol, xylitol, erythritol, maltitol, starch, acacia gum, alginate, gelatin, calcium phosphate, calcium silicate, cellulose, methylcellulose, microcrystalline cellulose, polyvinyl pyrrolidone, water, methyhydroxybenzoate, propylhydroxybenzoate, talc, magnesium stearate, and mineral oil.

In addition, the antibacterial composition of the present invention can be formulated into various oral dosage forms, such as powders, granules, tablets, capsules, suspensions, emulsions, syrups, airosols, etc., or parenteral dosage forms such as external use agents, suppositories, sterile injections, etc. In this regard, the pharmaceutical composition of the present invention may be formulated in combination with a diluent or excipient such as a filler, a thickener, a binder, a wetting agent, a disintegrant, a surfactant, etc. Solid preparations intended for oral administration may be in the form of, but not limited to, tablets, pills, powders, granules, capsules, and the like. In regards to these solid agents, the compound of Chemical Formula 1 or 2 is formulated in combination with at least one excipient such as starch, calcium carbonate, sucrose, lactose, or gelatin. In addition to a simple excipient, a lubricant such as magnesium stearate, talc, etc. may be used. Among liquid preparations intended for oral administration are suspensions, internal use solutions, emulsions, syrups, and the like, but they are not limited thereto. In addition to a simple diluent such as water or liquid paraffin, various excipients, such as wetting agents, sweeteners, aromatics, preservatives, and the like are encompassed in the scope of the liquid preparations. Also, the pharmaceutical composition of the present invention may be in a parenteral dosage form such as sterile aqueous solutions, non-aqueous solvents, suspensions, emulsions, lyophilizates, suppositories, and the like. Propylene glycol, polyethylene glycol, vegetable oils such as olive oil, and injectable esters such as ethyl oleate may be suitable as non-aqueous solvents and suspensions. The basic materials of suppositories include Witepsol, macrogol, Tween 61, cacao butter, laurin butter, and glycerogelatin.

Moreover, the antibacterial composition of the present invention may be administered orally or parenterally (e.g., intravenously, subcutaneously, intraperitoneally, or topically) according to need, and the dose of the pharmaceutical composition of the present invention may vary depending on various factors including patient's health and weight, the severity of disease, the form of drug, the route of administration, and the time of administration. The formulations of the compound may be administered in a single dose or may be divided into multiple doses. Also, the composition of the present invention may be used alone, or in combination with surgery, hormone therapy, pharmacotherapy, or biological response controllers so as to exhibit prophylactic and therapeutic effects on diseases caused by pathogenic bacteria and resistant bacteria.

Preferably, the antibacterial composition of the present invention may be a quasi-drug composition. Accordingly, the present invention envisages a quasi-drug composition for the prevention or improvement of infectious diseases caused by pathogenic microbes or resistant bacteria.

When used as a quasi-drug additive, the composition of the present invention may be viably used as-is, or in combination with another quasi-drug or quasi-drug component using a typical method. Its amount in the mixture may be properly determined depending on the purpose of use (prevention, sanitation or therapeutic treatment). Examples of the quasi-drug to which the composition of the present invention may be applied include, but are not limited to, disinfectants, shower foams, mouthwash, wet tissues, detergent soap, handwash, humidifier fillers, masks, ointments, or a filter coating.

In accordance with a further aspect thereof, the present invention provides a method for preventing or treating an infectious disease caused or triggered by a microbe, comprising administering a therapeutically effective amount of the antibacterial composition to a subject in need thereof. In this context, the microbe is a pathogenic microbe or a bacterium resistant to a conventional antibiotic.

As used herein, the term "prevention" is intended to refer to any action resulting in the suppression or delay of the onset of infectious diseases caused by pathogenic microbes or resistant bacteria owing to the administration of the composition according to the present invention. The term "treatment" is intended to refer to any action resulting in improvements in symptoms of pathogenic microbe- or resistant bacterium-caused infectious diseases or the beneficial alteration of the infectious disease state owing to the administration of the composition according to the present invention. The term "subject," as used herein, means an animal, including humans, which has been attacked with or is apt to be attacked by a pathogenic microbe- or resistant bacterium-caused infectious disease. Therefore, administration of the composition according to the present invention can effectively prevent or treat the above-mentioned diseases.

In the present invention, the pathogenic microbe is a microorganism that penetrates into and infects animal or plant bodies, causing a disease therein or damage thereto. In the context of the present invention, the pathogenic microbe includes bacteria, whether Gram-negative or positive, yeast, and fungi, and is preferably *Staphylococcus aureus, Staphylococcus epidermis, Bacillus subtilis, Bacillus cereus, Enterococcus faecium*, or *Candida albicans*.

As used herein, the term "resistant bacteria" refers to bacteria which are able to survive after exposure to antibiotics as a consequence of the constant use of antibiotics to treat or prevent a disease or a complication thereof, or a bacterial disorder or a complication thereof. Examples of the antibiotics include vancomycin, cephalosporin, quinolone, fluoroquinolone, penicillin, bata-lactamase inhibitors, carbapenem, monobactam, macrolide, lincomycin, glycopeptides, rifampin, oxazolidinone, tetracycline, aminoglycoside, streptogramin, and sulfonamide. Even after exposure to these antibiotics, the resistant bacteria survive, keeping diseases active in the subject. Preferably, the resistant bacteria may be methicillin-resistant *Staphylococcus aureus* (MRSA), quinolone-resistant *Staphylococcus aureus* (QRSA), vancomycin-resistant *Staphylococcus aureus* (VRSA) or vancomycin-resistant *Enterococcus* (VRE), with greater preference for vancomycin-resistant *Staphylococcus aureus* (VRSA) or vancomycin-resistant *Enterococcus* (VRE).

Also, in accordance with a still further aspect of the present invention, is a method for sterilizing a microbe or halting growth of a microbe, comprising applying the antibacterial composition in vitro. The microbes are pathogenic microbes or resistant bacteria.

As used herein, the term "sterilizing" means killing microbes such as pathogenic microbes or resistant bacteria, and the term "halting," as used in the context of the growth of microbes, means suppressing the growth and proliferation of microbes, such as pathogenic microbes or resistant bacteria.

Preferably, the microbe may be any one or more selected from the group consisting of *Staphylococcus aureus, Bacillus subtilis, Bacillus cereus, Staphylococcus epidermis, Enterococcus faecium*, methicillin-resistant *Staphylococcus aureus* (MRSA), quinolone-resistant *Staphylococcus aureus* (QRSA), vancomycin-resistant *Staphylococcus aureus*, and vancomycin-resistant *Enterococcus*.

In accordance with still another aspect thereof, the present invention addresses a method for producing a compound represented by Chemical Formula 1 or 2, or an isomer, derivative or pharmaceutically acceptable salt thereof, comprising allowing *Streptomyces* sp. AN1542 (Accession No.: KCTC 12113BP) to produce the compound represented by Chemical Formula 1 or 2.

Preferably, the method may comprise the following steps:

1) culturing *Streptomyces* sp. AN1542 (Accession No.: KCTC 12113BP) or a mutant thereof;

2) extracting the cell culture medium or mycelium of step 1) with an organic solvent and then with ethyl acetate; and 3) isolating the compound represented by Chemical Formula 1 or 2 from the ethyl acetate extract of step 2) by chromatography.

In step 1), in lieu of *Streptomyces* sp. AN1542 strain (Accession No.: KCTC 12113BP), a mutant derived therefrom (a natural mutant or an artificial mutant), a zygote thereof, or a novel strain created therefrom by genetic manipulation may be used.

*Streptomyces* sp. AN1542 strain (Accession No.: KCTC 12113BP) or a mutation thereof is cultured in a medium containing nutrients available for typical microorganisms. The nutrients may be those used for culturing fungi. For example, glucose, starch syrup, dextrin, starch, molasses, animal oils, or vegetable oils can be used as a carbon source. Examples of a nitrogen source useful in the present invention include wheat bran, soybean meal, wheat, malt, cotton seed meal, fish scraps, corn steep liquor, meat extract, a yeast extract, ammonium sulfate, niter, and urea. If necessary, the medium may contain a culinary salt, potassium, magnesium, cobalt, chlorine, phosphoric acid, sulfuric acid, and other inorganic salts productive of other ions to effectively grow the cells. They may be cultured in an aerobic condition with agitation or in a stationary manner.

The temperature at which the cells are cultured may slightly differ from one condition to another, and ranges typically from 20 to 37° C., and is, for the most part, between 26 and 30° C. In addition, the production of complestatin or neuroprotectin A was found to attain a maximum peak at a culture duration of 7 to 10 days, for both agitation and stationary cultures.

Step 2) is configured to extract complestatin or neuroprotectin A from a cell culture or mycelium of *Streptomyces* sp. AN1542 (Accession No.: KCTC 12113BP) or a mutant thereof. Complestatin or neuroprotectin A are in the mycelium as well as the cell culture medium. Accordingly, the ingredient of interest is extracted from the cell culture medium or mycelium using an organic solvent, such as acetone, and concentrated by evaporating acetone in a vacuum. Then, the concentrate was extracted with ethyl acetate, followed by removing the ethyl acetate solvent in a vacuum.

Step 3) is configured to separate the compounds of the present invention. The purification and isolation of the compounds of the present invention could be achieved using a method that is known in the art, without limitation. It is apparent to those skilled in the art that it is possible to control the amount and yield of the compounds, if necessary, by modifying the kinds of the medium used, culture conditions, and extraction and purification methods. In one embodiment, the compounds of the present invention were purified from the ethyl acetate extract through chromatography in the following manner.

The ethyl acetate concentrate obtained in step 2) was subjected to silica gel column chromatography using a mixture of chloroform:ethanol ranging from 100:1 to 1:1. Active fractions thus obtained were further purified by Sephadex LH-20 column chromatography using methanol as an eluent, followed by HPLC to two pure compounds, complestatin and neuroprotectin A (Example 3).

MODE FOR INVENTION

A better understanding of the present invention may be obtained through the following examples which are set forth to illustrate, but are not to be construed as limiting the present invention.

Example 1: Isolation of *Streptomyces* Sp. AN1542 Strain

To screen for strains producing a material with antibacterial activity against resistant bacteria, bacteria, fungi, and actinomyces, strains were isolated from soil across South Korea, and of them, a 1542 strain to have potent antibacterial activity was isolated. The 1542 strain producing complestatin and neuroprotecting A was found to have a typical morphology of actinomyces as observed by microscopy. For the 1542 strain, its whole genome was separated, and used to clone 16S ribosomal DNA by PCR. Analysis of the full sequence of the rRNA identified the strain as a *Streptomyces*, which was called *Streptomyces* sp. AN1542 and deposited with KCTC (the Korean Collection for Type Cultures) of the Korea Research Institute of Bioscience and Biotechnology (KRIBB) on Jan. 3, 2012 (Accession No.: KCTC 12113BP).

Example 2: Culturing of *Streptomyces* Sp. AN1542 Strain

For culturing *Streptomyces* sp. AN1542 strain, a seed medium containing water-soluble starch 1%, glucose 2%, soybean meal 2.5%, meat extract 0.1%, a yeast extract 0.4%, salt 0.2%, and a trace amount of potassium phosphate dibasic, pH 7.3 was employed.

After being autoclaved at 121° C. for 20 min, 20 ml of the seed medium in a 100 ml Erlenmeyer was inoculated with one platinum loop taken form a slant culture of *Streptomyces* sp. AN1542, and incubated at 28° C. for 3 days with agitation. This was used as a primary seed culture medium. Then, the seed culture was inoculated into 500 ml-Erlenmeyer flasks (48 ea.), and cultured at 28° C. for 7 to 12 days with agitation.

Example 3: Isolation and Purification of Compounds of Interest

An acetone extract of the cell culture medium and mycelium cultured in Example 2 was extracted three times with ethyl acetate in an acidic condition. The ethyl acetate layer containing the active ingredients was concentrated in a vacuum to remove ethyl acetate and then, subjected to silica gel column chromatography using a solvent mixture of chloroform:methanol ranging from 100:1 to 1:1. The active fractions thus obtained were further purified by Sephadex LH-20 column chromatography using methanol as an eluent, followed by HPLC to two pure compounds, complestatin and neuroprotectin A.

Physicochemical properties of complestatin and neuroprotectin A, isolated from *Streptomyces* sp. AN1542 strain, were as follows:

[Compound 1: Complestatin]
1) High resolution ESI-MS: 661.5490 m/z [M-2H]2-, $C_{61}H_{45}N_7O_{15}Cl_6$ requires 661.5480;
2) Molecular Formula: $C_{61}H_{45}Cl_6N_7O_{15}$;
3) Degree of polarization: [a]D=42.7° (c0.14, DMSO);
4) Nuclea Magnetic Resonance (NMR) Data: $^1H$ and $^{13}C$ NMR data measured at dimethyl sulfoxide (DMSO-d6) are summarized in Tables 1 and 2, below.

TABLE 1

Comparison between $^1$H-NMR data and reported values measured at DMSO-d6 of Complestatin

| Position | 1[a] | 2[b] |
|---|---|---|
| A | | |
| 1 | | |
| 2 | 6.86 (8.0) | 7.11 (8.0) |
| 3 | 6.63 (8.0) | 6.77 (9.2) |
| 4 | | |
| 5 | 6.63 (8.0) | 6.77 (9.2) |
| 6 | 6.86 (8.0) | 7.11 (8.0) |
| C=O | | |
| CH | 4.67 | 5.01 (7.2) |
| NH | 7.88 | 8.51 (6.3) |
| B | | |
| 1 | | |
| 2 | 7.17 (2.0, 8.5) | 7.19 (2.0, 8.6) |
| 3 | 7.08 (2.0, 8.0) | 7.08 (2.5, 7.0) |

TABLE 1-continued

Comparison between $^1$H-NMR data and reported values measured at DMSO-d6 of Complestatin

| Position | 1[a] | 2[b] |
|---|---|---|
| 4 | | |
| 5 | 6.84 (2.0, 9.0) | 6.87 (2.6, 8.2) |
| 6 | 7.86 (2.0, 9.0) | 7.83 (2.0, 8.8) |
| C=O | | |
| CH | 5.01 | 5.01 (7.2) |
| CH2 | 2.98, 3.24 | 3.05 |
| NCH3 | 2.9(s) | 2.99 |
| C | | |
| 1 | | |
| 2 | 7.33(s) | 7.34 |
| 3 | | |
| 4 | | |
| 5 | | |
| 6 | 7.33(s) | 7.34 |
| C=O | | |
| CH | 5.06 | 5.20 (7.0) |
| NH | 8.62 | 8.74 (6.2) |
| D | | |
| 1 | | |
| 2 | 5.49 (2.5) | 5.48 (4.0) |
| 3 | | |
| 4 | | |
| 5 | 5.07 (2.5) | 5.11 (3.5) |
| 6 | | |
| C=O | 5.53 | 5.56 (8.4) |
| CH | 8.21 (9.0) | 8.29 (9.2) |
| NH | | |
| E | | |
| 1 | | |
| 2 | 7.26 | 7.31 |
| 3 | | |
| 4 | | |
| 5 | 7.26 | 7.31 |
| 6 | | |
| C=O | 5.55 | 5.56 (8.4) |
| CH | 7.24 (8.5) | 7.88 (7.8) |
| NH | | |
| F | | |
| 1 | 10.88(s) | 10.9 |
| 2 | 7.27 | 7.27 (2.8) |
| 3 | | |
| 3[a] | | |
| 4 | 7.45 (8.5) | 7.44 (9.0) |
| 5 | 6.81 (8.5) | 6.83 (1.5, 8.2) |
| 6 | | |
| 7 | 7.24(s) | 7.30 |
| 7[a] | | |
| C=O | | |
| CH | 4.11(m) | 4.18 |
| CH2 | 2.86, 3.39 | 2.89, 3.5 |
| NH | 8.27 (7.0) | 8.86 (6.8) |
| G | | |
| 1 | | |
| 2 | 7.78(s) | 7.78 |
| 3 | | |
| 4 | | |
| 5 | | |
| 6 | 7.78(s) | 7.78 |
| aC=O | | |
| bC=O | | |

[a]$^1$H and $^{13}$C NMR spectral data were measured in DMSO-d6 at 500 MHz and 125 MHz, respectively.
[b]Note: Tet. Lett. 30: 4987-4990, 1989

TABLE 2

Comparison between ¹³H-NMR data and reported values measured at DMSO-d6 of Complestatin

| Position | 1 | 2 |
|---|---|---|
| A | | |
| 1 | 131.4 | 127.8 |
| 2 | 127.5 | 128.2 |
| 3 | 114.5 | 115.3 |
| 4 | 155.6 | 157.1 |
| 5 | 114.5 | 115.3 |
| 6 | 127.5 | 128.2 |
| C=O | 171.2 | 171.3 |
| CH | 57.6 | 55.8 |
| NH | | |
| B | | |
| 1 | 134.6 | 134.5 |
| 2 | 130.4 | 131.5 |
| 3 | 121.7 | 121.7 |
| 4 | 155.1 | 155.2 |
| 5 | 123.1 | 123.7 |
| 6 | 131.6 | 130.6 |
| C=O | 168.5 | 168.4 |
| CH | 61.9 | 61.3 |
| CH2 | 34.3 | 35.0 |
| NCH3 | 31.0 | 31.2 |
| C | | |
| 1 | 131.1 | 131.0 |
| 2 | 127.2 | 127.0 |
| 3 | 122.1 | 122.0 |
| 4 | 149.8 | 148.7 |
| 5 | 122.1 | 122.0 |
| 6 | 127.2 | 127.0 |
| C=O | 169.2 | 169.2 |
| CH | 51.9 | 51.5 |
| NH | | |
| D | | |
| 1 | 126.3 | 126.4 |
| 2 | 110.7 | 110.5 |
| 3 | 149.0 | 149.6 |
| 4 | 139.0 | 139.4 |
| 5 | 131.0 | 131.1 |
| 6 | 129.4 | 129.5 |
| C=O | 167.5 | 167.6 |
| CH | 54.9 | 55.0 |
| NH | | |
| E | | |
| 1 | 131.9 | 131.9 |
| 2 | 126.7 | 126.7 |
| 3 | 121.7 | 121.7 |
| 4 | 149.0 | 148.1 |
| 5 | 121.7 | 121.7 |
| 6 | 126.7 | 126.7 |
| C=O | 169.5 | 169.8 |
| CH | 54.7 | 55.2 |
| NH | | |
| F1 | 123.5 | 123.6 |
| 2 | 111.7 | 111.5 |
| 3 | 126.0 | 126.3 |
| 3a | 118.4 | 118.4 |
| 4 | 123.6 | 123.7 |
| 5 | 134.6 | 134.4 |
| 6 | 114.4 | 114.4 |
| 7 | 136.1 | 136.3 |
| 7a | 170.4 | 170.3 |
| C=O | 56.9 | 57.1 |
| CH | 28.4 | 28.2 |
| CH2 | | |
| NH | | |
| G | 127.2 | 124.1 |
| 1 | 130.6 | 130.1 |
| 2 | 122.5 | 122.5 |
| 3 | 166.7 | 155.8 |
| 4 | 122.5 | 122.5 |
| 5 | 130.6 | 130.1 |
| 6 | 181.6 | 185.7 |
| aC=O | 164.5 | 163.7 |
| bC=O | | |

¹H and ¹³C NMR spectral data were measured in DMSO-d6 at 500 MHz and 125 MHz, respectively.
Note:
Tet. Lett. 30: 4987-4990, 1989

5) Structural Formula

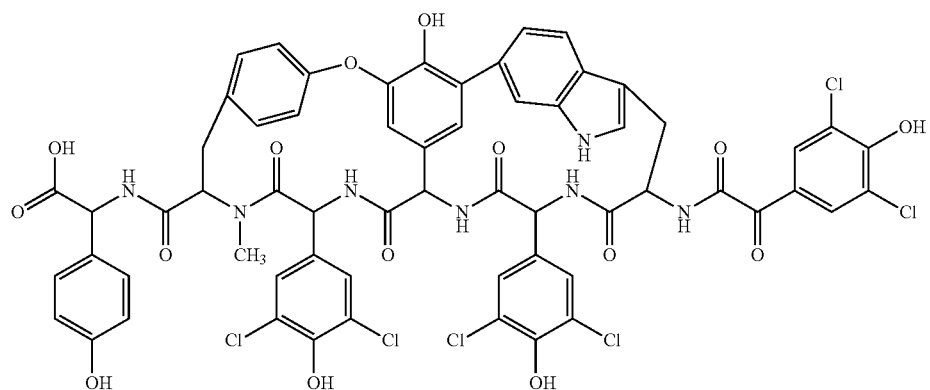 [SMILES: CN1C(=O)C(c2cc(Cl)c(O)c(Cl)c2)NC(=O)C2NC(=O)C(c3cc(Cl)c(O)c(Cl)c3)NC(=O)C(NC(=O)C(=O)c3cc(Cl)c(O)c(Cl)c3)Cc3c[nH]c4cc(ccc34)-c3cc2cc(c3O)Oc2ccc(cc2)CC1C(=O)NC(C(=O)O)c1ccc(O)cc1]

[Compound 2: Neuroprotectin A]

1) Molecular Weight: 1341.1;
2) Molecular Formula: $C_{61}H_{45}Cl_6N_7O_{16}$;
3) Nuclear Magnetic Resonance (NMR) data: ¹H-¹H COSY and HMBC NMR data measured at dimethyl sulfoxide (DMSO-d6) are summarized in FIGS. 1 and 2.

4) Structural Formula

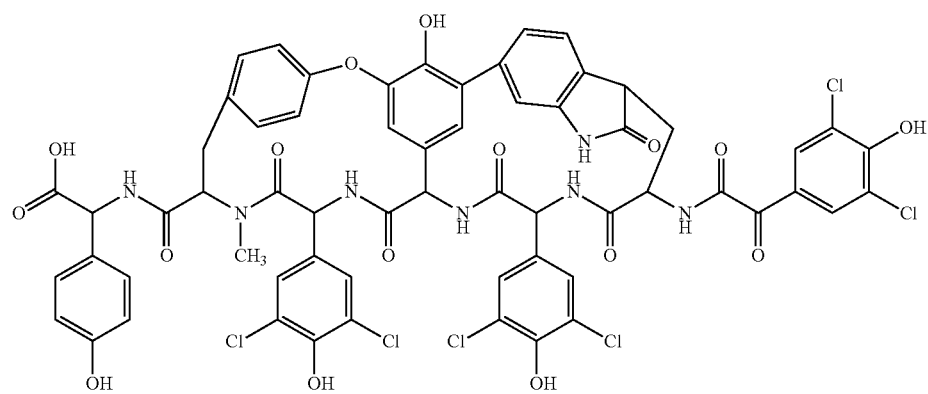 [SMILES: CN1C(=O)C(c2cc(Cl)c(O)c(Cl)c2)NC(=O)C2NC(=O)C(c3cc(Cl)c(O)c(Cl)c3)NC(=O)C(NC(=O)C(=O)c3cc(Cl)c(O)c(Cl)c3)CC3C(=O)Nc4cc(ccc43)-c3cc2cc(c3O)Oc2ccc(cc2)CC1C(=O)NC(C(=O)O)c1ccc(O)cc1]

Example 4: Measurement for Antibacterial Activity of Complestatin and Neuroprotectin A To examine complestatin and neuroprotectin A for antibacterial activity, the following experiment was performed. Test strains were maintained in MHB (Mueller Hinton broth), and antibacterial activity was measured using a broth microdilution method. After being incubated overnight, each of the test stains was diluted to a population of 2×100,000 cells/ml, and aliquoted in an amount of 100 μl per well into 96-well plates. Complestatin, neuroprotectin A and positive controls such as vancomycin, oxacillin and nofloxacin were treated at concentration with gradual dilution by 2-fold from maximum concentration of 128 μg/ml. Each compound was diluted in dimethylsulxoside (DMSO), and the concentration of DMSO was adjusted to approximately 1/100 before application. After incubation for 20 hrs, absorbance was read at 650 nm to examine the growth of bacterial cells. A minimum concentration of each of the compounds at which the growth of the bacteria was completely inhibited was determined as MIC (μg/ml), and the results are summarized in Table 3, below.

As a result, the compounds of the present invention complestatin and neuroprotectin A exhibited antibacterial activity identical or superior to that of vancomycin against *Staphylococcus aureus, Bacillus subtilis, Bacillus cereus, Enterococcus faecium* and *Staphylococcus epidermis* (MIC of 0.5-2 μg/ml), and specifically against methicillin-resistant *Staphylococcus aureus* (MRSA) and Quinolone-resistant *Staphylococcus aureus* (QRSA) (Table 3).

Example 5: Measurement for Antibacterial Activity of Complestatin and Neuroprotectin A Against Vancomycin-Resistant Bacteria The compounds of the present invention, complestatin and neuroprotectin A were examined for antibacterial activity against vacomycin-resistant bacteria in the same manner as in Example 4, and the results are given in Table 4, below.

TABLE 3

| Test Strain | Complestatin | Neuroprotectin A | Vancomycin | Oxacillin | Norfloxacin |
|---|---|---|---|---|---|
| *Staphylococcus aureus* 209 | 2 | 2 | 0.5 | 0.25 | 0.25 |
| *Staphylococcus aureus* RN 4220 | 1 | 1 | 1 | 0.25 | 1 |
| MRSA CCARM 3167 | 1 | 1 | 2 | 500 | 8 |
| MRSA CCARM 3506 | 1 | 1 | 0.5 | 500 | 1 |
| QRSA CCARM 3505 | 1 | 1 | 1 | 0.5 | 250 |
| QRSA CCARM 3519 | 2 | 2 | 1 | 0.5 | 125 |
| *Bacillus subtilis* KCTC 1021 | 0.5 | 0.5 | 0.125 | 0.25 | 0.25 |
| *Bacillus cereus* KCTC 1661 | 0.5 | 0.5 | 1 | 32 | 1 |
| *Entercoccus faecium* KCTC 5191 | 2 | 2 | 1 | 4 | 4 |
| *Entercoccus faecium* KCTC 3511 | 2 | 2 | 2 | 8 | 4 |
| *Staphylococcus epidermidis* KCTC 3958 | 2 | 2 | 2 | 0.25 | 0.5 |

| | Complestatin | Neuroprotectin A | Vancomycin | Oxacillin | Norfloxacin |
|---|---|---|---|---|---|
| S. aureus RN 4220 | 1 | 1 | 1 | 0.25 | 1 |
| VRSA 48 | 1 | 1 | >200 | >200 | 200 |
| VRE 11 | 1 | 1 | >200 | >200 | 200 |
| VRE 7 | 1 | 1 | >200 | >200 | 50 |
| VRE 3 | 1 | 1 | >200 | >200 | 50 |

As can be seen in Table 4, complestatin and neuroprotectin A exhibited strong antibacterial activity against the vancomycin resistant bacteria Vancomycin-resistant *S. aureus* (VRSA) and Vancomycin-resistant *Enterococcus* (VRE) with an MIC of 1 μg/ml whereas neither vancomycin nor oxacillin exhibited antibacterial activity even at 200 μg/ml against vancomycin resistant bacteria VRSA and VRE.

Taken together, the results obtained above suggest that complestatin and neuroprotectin A inhibit the growth of bacteria using a mechanism different from that of vancomycin, thus effectively exerting antibacterial activity on vancomycin-resistant bacteria, so-called superbacteria.

The invention claimed is:

1. An antibacterial composition, comprising a compound represented by the following Chemical Formula 1 or pharmaceutically acceptable salt thereof; and a compound represented by the following Chemical Formula 2 or pharmaceutically acceptable salt thereof:

[Chemical Formula 1]

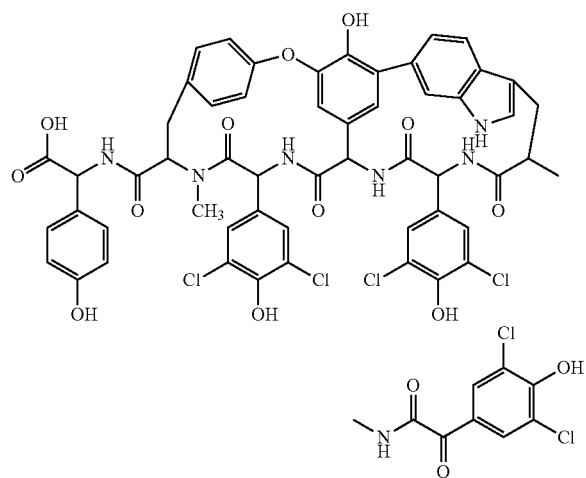

[Chemical Formula 2]

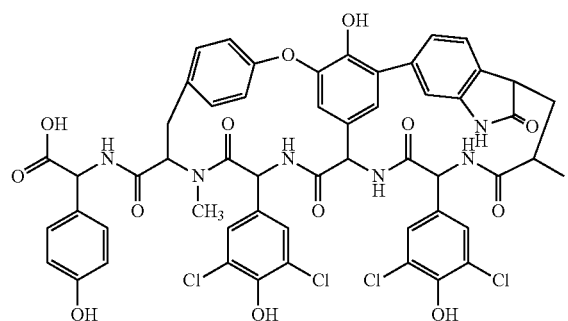

-continued

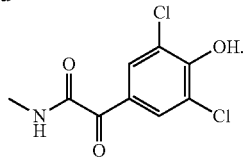

2. The antibacterial composition of claim 1, wherein the compound represented by the Chemical Formula 1 and the compound represented by the Chemical Formula 2 are produced from *Streptomyces* sp. AN1542 strain (Accession No.: KCTC 12113BP).

3. The antibacterial composition of claim 1, exhibiting antibacterial activity against any one or more selected from the group consisting of *Staphylococcus aureus, Bacillus subtilis, Bacillus cereus, Staphylococcus epidermis, Enterococcus faecium*, Methicillin-resistant *Staphylococcus aureus* (MRSA), Quinolone-resistant *Staphylococcus aureus* (QRSA), Vancomycin-resistant *Staphylococcus aureus*, and Vancomycin-resistant *Enterococcus*.

4. The antibacterial composition of claim 1, being in a form of a pharmaceutical composition.

5. A method for treating an infectious disease caused or triggered by a microbe, comprising administering a therapeutically effective amount of the antibacterial composition of claim 1 to a subject in need thereof.

6. The method of claim 5, wherein the microbe is any one or more Selected from the group consisting of *Staphylococcus aureus, Bacillus subtilis, Bacillus cereus, Staphylococcus epidermis, Enterococcus faecium*, Methicillin-resistant *Staphylococcus aureus* (MRSA), Quinolone-resistant *Staphylococcus aureus* (QRSA), Vancomycin-resistant *Staphylococcus aureus* and Vancomycin-resistant *Enterococcus*.

7. A method for sterilizing a microbe or halting growth of a microbe, comprising applying the antibacterial composition of claim 1 in vitro.

8. The method of claim 7, wherein the microbe is any one or more selected from the group consisting of *Staphylococcus aureus, Bacillus subtilis, Bacillus cereus, Staphylococcus epidermis, Enterococcus faecium*, Methicillin-resistant *Staphylococcus aureus* (MRSA), Quinolone-resistant *Staphylococcus aureus* (QRSA), Vancomycin-resistant *Staphylococcus aureus* and Vancomycin-resistant *Enterococcus*.

9. A method for producing a compound represented by Chemical Formula 1 or 2, or pharmaceutically acceptable salt thereof, comprising allowing *Streptomyces* sp. AN1542 strain (Accession No.: KCTC 12113BP) to produce the compound represented by following Chemical Formula 1 or 2:

[Chemical Formula 1]

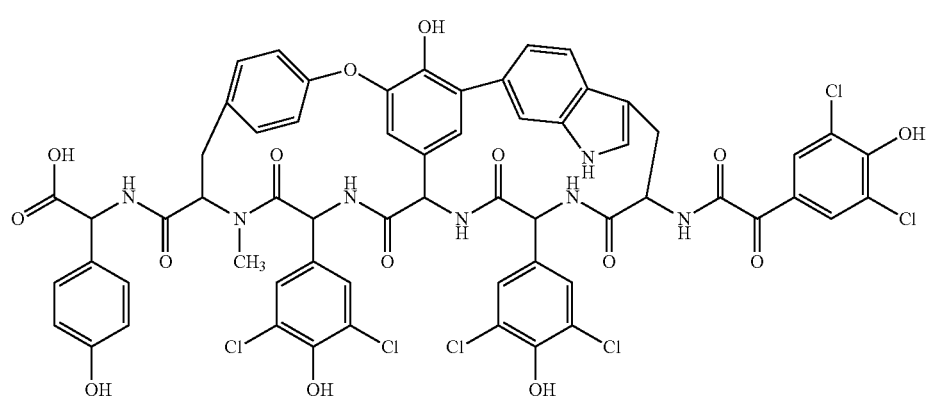

[Chemical Formula 2]

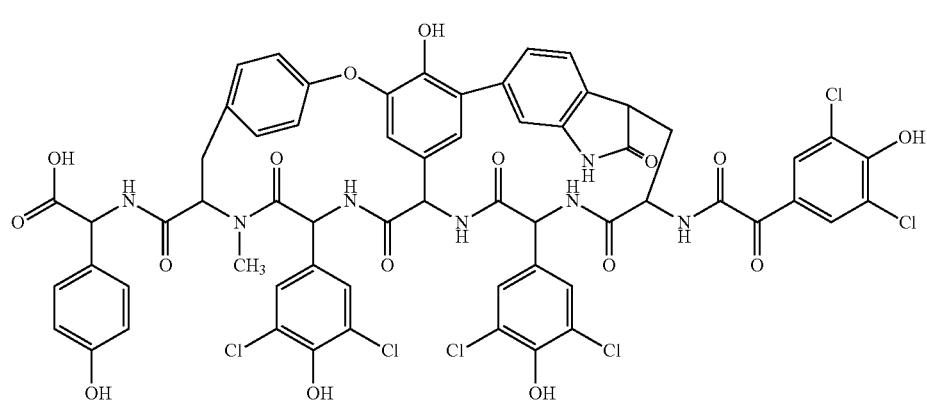

and recovering the compound or pharmaceutically acceptable salt.

10. The method of claim 9, comprising:
1) culturing *Streptomyces* sp. AN1542 strain (Accession No.: KCTC 12113BP) or a mutant thereof;
2) extracting the cell culture medium or mycelium of step 1) with an organic solvent and then with ethyl acetate; and
3) isolating the compound represented by Chemical Formula 1 or 2 from the ethyl acetate extract of step 2) by chromatography.

* * * * *